(12) United States Patent
Lee et al.

(10) Patent No.: US 12,178,439 B2
(45) Date of Patent: Dec. 31, 2024

(54) EMBOLIC DEVICES FOR OCCLUDING BODY LUMENS

(71) Applicants: STRYKER CORPORATION, Kalamazoo, MI (US); STRYKER EUROPEAN OPERATIONS LIMITED, Carrigtwohill (IE)

(72) Inventors: Andrew S. Lee, San Jose, CA (US); Clifford Teoh, Los Altos, CA (US); Hancun Chen, San Ramon, CA (US); Jinhoon Park, San Jose, CA (US)

(73) Assignees: Stryker Corporation, Kalamazoo, MI (US); Stryker European Operations Limited, Carrigtwohill (IE)

( * ) Notice: Subject to any disclaimer, the term of this patent is extended or adjusted under 35 U.S.C. 154(b) by 129 days.

(21) Appl. No.: 16/679,641

(22) Filed: Nov. 11, 2019

(65) Prior Publication Data

US 2021/0137526 A1    May 13, 2021

(51) Int. Cl.
*A61B 17/12* (2006.01)
*A61B 17/00* (2006.01)
*A61M 25/01* (2006.01)

(52) U.S. Cl.
CPC .. *A61B 17/12113* (2013.01); *A61B 17/00234* (2013.01); *A61B 17/12168* (2013.01);
(Continued)

(58) Field of Classification Search
CPC .......... A61B 17/12113; A61B 17/1214; A61B 17/12145; A61B 17/12168;
(Continued)

(56) References Cited

U.S. PATENT DOCUMENTS

| | | | | |
|---|---|---|---|---|
| 5,354,295 A | * | 10/1994 | Guglielmi | A61B 17/12113 606/41 |
| 5,649,949 A | * | 7/1997 | Wallace | A61B 17/1215 606/198 |

(Continued)

FOREIGN PATENT DOCUMENTS

| | | |
|---|---|---|
| EP | 0743047 | 11/1996 |
| EP | 2932921 | 10/2015 |

(Continued)

OTHER PUBLICATIONS

PCT International Search Report and Written Opinion for International Appln. No. PCT/US2020/059494, Applicant Stryker Corporation, dated Feb. 24, 2021 (13 pages).

(Continued)

*Primary Examiner* — Todd J Scherbel
(74) *Attorney, Agent, or Firm* — Vista IP Law Group, LLP (57) ABSTRACT

An embolic device for placement in a body lumen, includes: a first segment having a first linear configuration when located inside a catheter, the first segment being configured to form a first three-dimensional structure when outside the catheter, wherein the first three-dimensional structure defines a cavity; and a second segment extending from the first segment, the second segment having a second linear configuration when located inside the catheter, the second segment being configured to form a second three-dimensional structure when outside the catheter; wherein the cavity of the first three-dimensional structure is configured to accommodate at least a majority of the second three-dimensional structure.

20 Claims, 6 Drawing Sheets

(52) U.S. Cl.
CPC ... *A61B 17/12172* (2013.01); *A61M 25/0133* (2013.01); *A61B 2017/00292* (2013.01); *A61M 2025/0163* (2013.01)

(58) Field of Classification Search
CPC ........ A61B 17/12172; A61B 17/00234; A61B 2017/00292
See application file for complete search history.

(56) References Cited

U.S. PATENT DOCUMENTS

| | | | | |
|---|---|---|---|---|
| 5,749,891 | A * | 5/1998 | Ken | A61B 17/12113 606/200 |
| 2006/0079926 | A1 * | 4/2006 | Desai | A61B 17/12022 606/200 |
| 2009/0112251 | A1 * | 4/2009 | Qian | A61B 17/12163 606/194 |
| 2013/0116722 | A1 * | 5/2013 | Aboytes | A61B 17/12172 606/198 |
| 2016/0317158 | A1 | 11/2016 | Lorenzo et al. | |
| 2017/0105738 | A1 | 4/2017 | Suzuki | |
| 2017/0189035 | A1 * | 7/2017 | Porter | A61B 17/12172 |
| 2018/0036012 | A1 | 2/2018 | Aboytes et al. | |
| 2018/0263630 | A1 * | 9/2018 | Tsukumo | A61B 17/12113 |

FOREIGN PATENT DOCUMENTS

| | | |
|---|---|---|
| JP | 2003230564 | 8/2003 |
| JP | 2010051475 | 3/2010 |
| JP | A 2016209575 | 12/2016 |
| WO | WO 9909893 | 3/1999 |
| WO | WO 2007/076179 | 7/2007 |

OTHER PUBLICATIONS

Foreign Notice of Rejection for JP Patent Appln. No. 2022-526759 dated May 21, 2024 (with English translation).
Foreign Notice of Rejection for JP Patent Appln. No. 2022-526759 dated Sep. 10, 2024 (with English translation).
Foreign Exam Report for EP Patent Appln. No. 20817144.7 dated Nov. 11, 2024.

* cited by examiner

EMBOLIC DEVICES FOR OCCLUDING BODY LUMENS

FIELD

The field of the disclosure relates to medical devices and methods for occluding body lumens, and more specifically, to medical devices and methods for occluding aneurysms.

BACKGROUND

An aneurysm is a dilation of a blood vessel that poses a risk to health from the potential for rupture, clotting, or dissecting. Rupture of an aneurysm in the brain causes stroke, and rupture of an aneurysm in the abdomen causes shock. Cerebral aneurysms are usually detected in patients as the result of a seizure or hemorrhage and can result in significant morbidity or mortality.

There are a variety of materials and devices which have been used for treatment of aneurysms, including platinum and stainless steel microcoils, polyvinyl alcohol sponges (Ivalone), and other mechanical devices. For example, vaso-occlusion devices are surgical implements or implants that are placed within the vasculature of the human body, typically via a catheter, either to block the flow of blood through a vessel making up that portion of the vasculature through the formation of an embolus or to form such an embolus within an aneurysm stemming from the vessel.

In some cases, there is a risk that known coil designs will migrate fully or partially out of the aneurysm entrance zone and into the feeding vessel. This risk is particularly high with wide neck aneurysms. Wide neck aneurysms are those in which the neck (the entrance zone) has a diameter that is at least 50% of the largest diameter of the aneurysm.

New embolic devices for occluding body lumens would be desirable.

SUMMARY

An embolic device for placement in a body lumen, includes: a first segment having a first linear configuration when located inside a catheter, the first segment being configured to form a first three-dimensional structure when outside the catheter, wherein the first three-dimensional structure defines a cavity; and a second segment extending from the first segment, the second segment having a second linear configuration when located inside the catheter, the second segment being configured to form a second three-dimensional structure when outside the catheter; wherein the cavity of the first three-dimensional structure is configured to accommodate at least a majority of the second three-dimensional structure.

Optionally, the first three-dimensional structure comprises a first loop, and the second three-dimensional structure comprises a second loop, Optionally, a first curvature of the first loop of the first three-dimensional structure is less than a second curvature of the second loop of the second three-dimensional structure.

Optionally, the first segment has a first width, and the second segment has a second width that is less than the first width; and/or wherein the first segment has a first thickness, and the second segment has a second thickness that is less than the first thickness.

Optionally, the first segment and the second segment form a unity configuration.

Optionally, each of the first segment and the second segment comprises a braided segment.

Optionally, the first three-dimensional structure comprises a first plurality of loops, and wherein loop widths, loop curvatures, braid widths, braid thicknesses, braid angles, or any combination of the foregoing, of the respective ones of the first plurality of loops increase or decrease along a length of the first segment forming the first three-dimensional structure; and/or wherein the second three-dimensional structure comprises a second plurality of loops, and wherein loop widths, loop curvatures, braid widths, braid thicknesses, braid angles, or any combination of the foregoing, of the respective ones of the second plurality of loops increase or decrease along a length of the second segment forming the second three-dimensional structure.

Optionally, the first three-dimensional structure comprises a first plurality of loops, and wherein angles between adjacent ones of the first plurality of loops increase or decrease along a length of the first segment forming the first three-dimensional structure; and/or wherein the second three-dimensional structure comprises a second plurality of loops, and wherein angles between adjacent ones of the second plurality of loops increase or decrease along a length of the second segment forming the second three-dimensional structure.

Optionally, the first three-dimensional structure is configured to provide a scaffolding across a neck of an aneurysm.

Optionally, the first three-dimensional structure has at least two adjacent loops with respective loop dimensions that do not vary by more than 20%, or that do not vary by more than 10%, or that do not vary by more than 5%.

Optionally, the first three-dimensional structure has at least two adjacent loops forming a first angle, and wherein the second three-dimensional structure has at least two adjacent loops forming a second angle that is less than the first angle.

Optionally, the first segment and the second segment are parts of an elongated member having a distal end and a proximal end.

An embolic device for placement in a body lumen, includes: an elongated member having a proximal end and a distal end; wherein the elongated member comprises a first segment configured to form a first three-dimensional structure, wherein the first three-dimensional structure defines a cavity; and wherein the elongated member comprises a second segment configured to form a second three-dimensional structure inside the cavity of the first three-dimensional structure.

Optionally, the first three-dimensional structure formed by the first segment of the elongated member comprises a first loop, and the second three-dimensional structure formed by the second segment of the elongated member comprises a second loop, Optionally, a first curvature of the first loop of the first three-dimensional structure is less than a second curvature of the second loop of the second three-dimensional structure.

Optionally, the first segment has a first width, and the second segment has a second width that is less than the first width; and/or wherein the first segment has a first thickness, and the second segment has a second thickness that is less than the first thickness.

Optionally, the first segment and the second segment form a unity configuration.

Optionally, each of the first segment and the second segment comprises a braided segment.

Optionally, the first three-dimensional structure comprises a first plurality of loops, and wherein loop widths, loop curvatures, braid widths, braid thicknesses, braid angles, or any combination of the foregoing, of the respective ones of the first plurality of loops increase or decrease along a length of the first segment forming the first three-dimensional structure; and/or wherein the second three-dimensional structure comprises a second plurality of loops, and wherein loop widths, loop curvatures, braid widths, braid thicknesses, braid angles, or any combination of the foregoing, of the respective ones of the second plurality of loops increase or decrease along a length of the second segment forming the second three-dimensional structure.

Optionally, the first three-dimensional structure comprises a first plurality of loops, and wherein angles between adjacent ones of the first plurality of loops increase or decrease along a length of the first segment forming the first three-dimensional structure; and/or wherein the second three-dimensional structure comprises a second plurality of loops, and wherein angles between adjacent ones of the second plurality of loops increase or decrease along a length of the second segment forming the second three-dimensional structure.

Optionally, the first three-dimensional structure is configured to provide a scaffolding across a neck of an aneurysm.

Optionally, the first three-dimensional structure has at least two adjacent loops with respective loop dimensions that do not vary by more than 20%, or do not vary by more than 10%, or that do not vary by more than 5%.

Optionally, the first three-dimensional structure has at least two adjacent loops forming a first angle, and wherein the second three-dimensional structure has at least two adjacent loops forming a second angle that is less than the first angle.

A method of occluding a body lumen includes: delivering a first segment of an embolic device into the body lumen, wherein the delivered first segment forms a first three-dimensional structure inside the body lumen, the first three-dimensional structure defines a cavity; and delivering a second segment of the embolic device into the body lumen, the second segment extending from the first segment, wherein the delivered second segment forms a second three-dimensional structure; wherein at least a majority of the second three-dimensional structure is accommodated in the cavity of the first three-dimensional structure.

Optionally, the first three-dimensional structure comprises a first loop, and the second three-dimensional structure comprises a second loop, Optionally, a first curvature of the first loop of the first three-dimensional structure is less than a second curvature of the second loop of the second three-dimensional structure.

Optionally, the first segment has a first width, and the second segment has a second width that is less than the first width; and/or wherein the first segment has a first thickness, and the second segment has a second thickness that is less than the first thickness.

Optionally, the first segment and the second segment form a unity configuration.

Optionally, each of the first segment and the second segment comprises a braided segment.

Optionally, the first three-dimensional structure comprises a first plurality of loops, and wherein loop widths, loop curvatures, braid widths, braid thicknesses, braid angles, or any combination of the foregoing, of the respective ones of the first plurality of loops increase or decrease along a length of the first segment forming the first three-dimensional structure; and/or wherein the second three-dimensional structure comprises a second plurality of loops, and wherein loop widths, loop curvatures, braid widths, braid thicknesses, braid angles, or any combination of the foregoing, of the respective ones of the second plurality of loops increase or decrease along a length of the second segment forming the second three-dimensional structure.

Optionally, the first three-dimensional structure comprises a first plurality of loops, and wherein angles between adjacent ones of the first plurality of loops increase or decrease along a length of the first segment forming the first three-dimensional structure; and/or wherein the second three-dimensional structure comprises a second plurality of loops, and wherein angles between adjacent ones of the second plurality of loops increase or decrease along a length of the second segment forming the second three-dimensional structure.

Optionally, the first three-dimensional structure provides a scaffolding across a neck of an aneurysm.

Optionally, the first three-dimensional structure has at least two loops with respective loop dimensions that do not vary by more than 20%, or that do not vary by more than 10%, or that do not vary by more than 5%.

Optionally, the first three-dimensional structure has at least two adjacent loops forming a first angle, and wherein the second three-dimensional structure has at least two adjacent loops forming a second angle that is less than the first angle.

Optionally, the first segment and the second segment are parts of an elongated member having a distal end and a proximal end.

Other and further aspects and features will be evident from reading the following detailed description.

DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only exemplary embodiments and are not therefore to be considered limiting in the scope of the claims.

DETAILED DESCRIPTION

Various embodiments are described hereinafter with reference to the figures. It should be noted that the figures are not drawn to scale and that elements of similar structures or functions are represented by the same reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Figure 1:
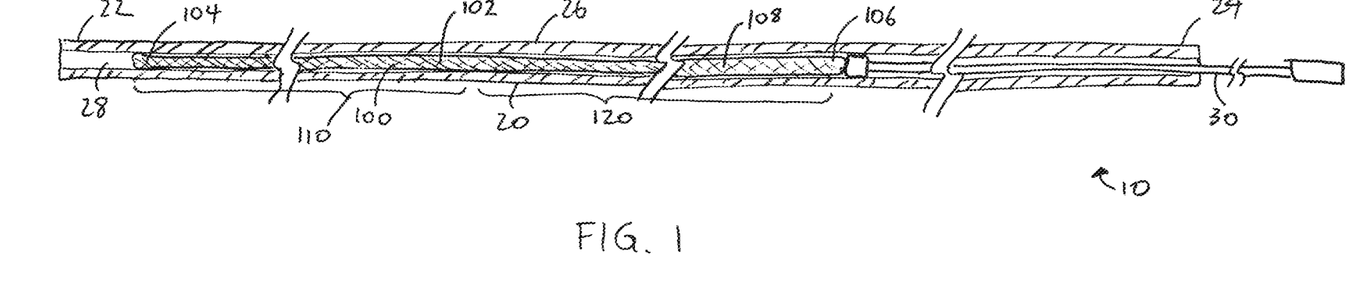
FIG. 1 illustrates a medical device having a catheter for delivering an embolic device.

FIG. 1 illustrates a medical device 10 having a catheter 20 for delivering an embolic device 100 in a body lumen. The catheter 20 has a distal end 22, a proximal end 24, and a catheter body 26 extending between the distal end 22 and the proximal end 24. The embolic device 100 is contained within a lumen 28 of the catheter 20. The catheter 20 further includes a shaft 30 located in the lumen 28 for pushing the embolic device 100 out of the lumen 28 of the catheter 20.

As shown in FIG. 1, the embolic device 100 is made from an elongated member 102 having a distal end 104, a proximal end 106, and a body 108 extending between the distal end 104 and the proximal end 106. The embolic device 100 has a first segment 110 having a first linear configuration when located inside the catheter 20. The first segment 110 is configured to form a first three-dimensional structure 112 when the first segment 110 is delivered outside the catheter 20 (FIG. 2A).

As also shown in FIG. 1, the embolic device 100 has a second segment 120 extending from the first segment 110. The second segment 120 is proximal with respect to the first segment 110. The second segment 120 has a second linear configuration when located inside the catheter 20. The second segment 120 is configured to form a second three-dimensional structure 122 when the second segment 120 is delivered outside the catheter 20 (FIG. 2B). In some embodiments, the first segment 110 and the segment 120 may be parts of a single structure that is formed to have the first segment 110 and the second segment 120. In other embodiments, the first segment 110 and the second segment 120 may be separate components that are connected together, e.g., via adhesive, weld, fusion, mechanical connector, etc. In either case, the first segment 110 and the second segment 120 may be considered as having or forming a unity configuration.

Figure 2A:
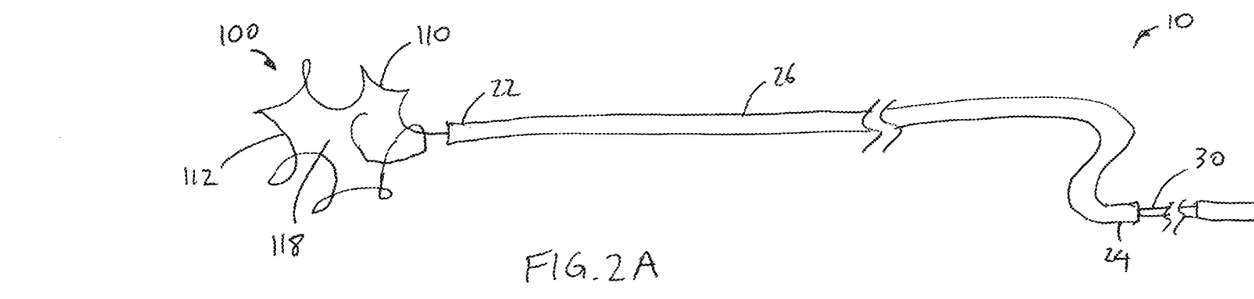
FIG. 2A illustrates the medical device of FIG. 1, particularly showing a distal segment of the embolic device being delivered out of the catheter.
Figure 2B:
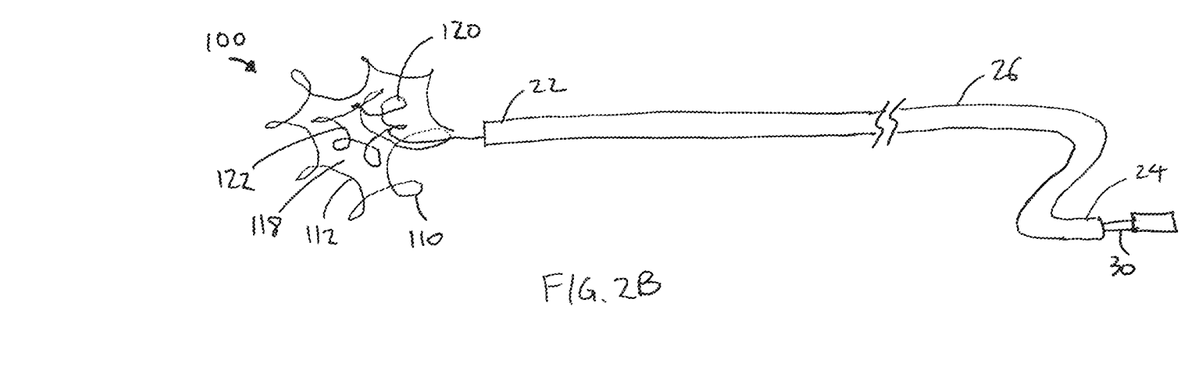
FIG. 2B illustrates the medical device of FIG. 1, particularly showing a proximal segment of the embolic device being delivered out of the catheter.

As shown in FIG. 2A, the first three-dimensional structure 112 defines a cavity 118 after the first segment 110 forming the first three-dimensional structure 112 is delivered out of the catheter 20. Accordingly, after the first segment 110 has been delivered out of the catheter 20 into a body lumen, the first three-dimensional structure 112 provides the cavity 118 for accommodating a remaining part (e.g., at least a majority of the second segment 120 forming the second three-dimensional structure 122) of the embolic device 100.

Figure 3:
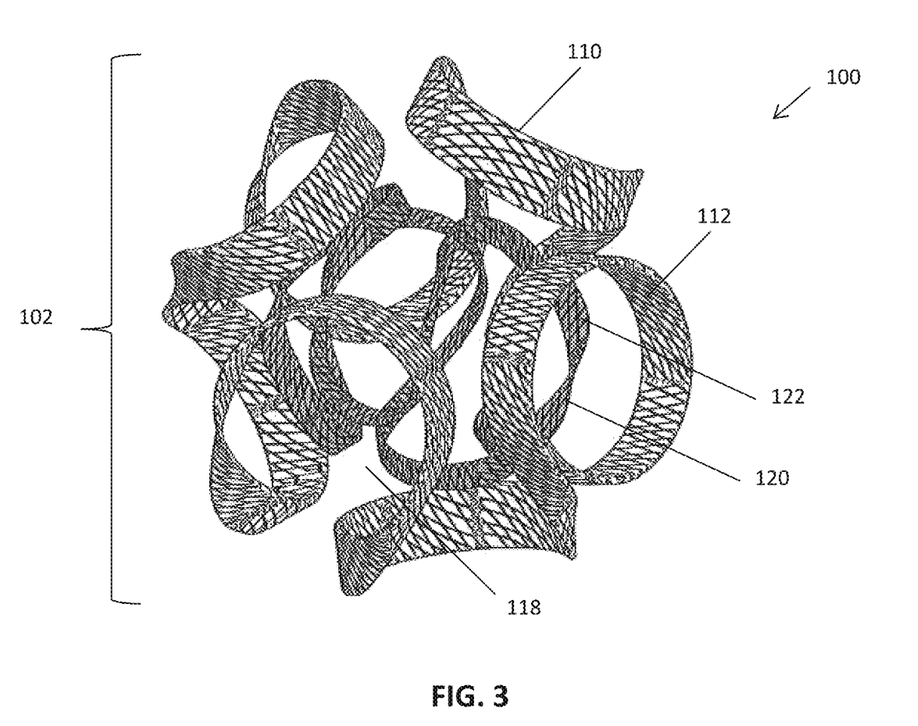
FIG. 3 illustrates the embolic device of FIG. 1, particularly showing the embolic device having a first segment forming a first three-dimensional structure, and a second segment forming a second three-dimensional structure inside the first three-dimensional structure.

FIG. 3 illustrates the embolic device 100 of FIG. 1, particularly showing the embolic device 100 having the first segment 110 forming the first three-dimensional structure 112, and the second segment 120 forming the second three-dimensional structure 122 inside the cavity 118 of first three-dimensional structure 112. As discussed, the first segment 110 and the second segment 120 are parts of the elongated member 102.

Figure 4A:
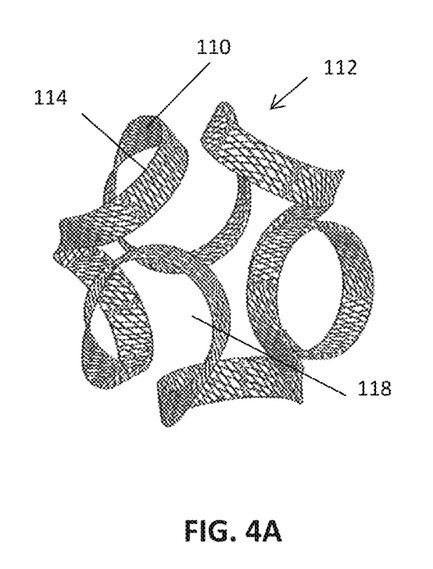
FIG. 4A illustrates the first three-dimensional structure of the embolic device of FIG. 1.

As shown in FIG. 4A, the first three-dimensional structure 112 comprises a series of seven (7) loops 114. The loops 114 may be open loops like that shown in the figure. Alternatively, one or more of the loops 114 may be closed-loops. In other embodiments, the first three-dimensional structure 112 may have more than seven loops (e.g., eight loops, nine loops, ten loops, eleven loops, twelve loops, etc.) or fewer than seven loops (e.g., six loops, five loops, four loops, etc.). In the illustrated embodiments, the loops of the first three-dimensional structure 112 are connected by respective inflection points, which allow adjacent loops 114 to form reverse curvatures. In other embodiments, adjacent loops 114 of the first three-dimensional structure 112 may not form reverse curvatures. Furthermore, in other embodiments, instead of loops, the first three-dimensional structure 112 may have other structural elements with shapes that are not loops.

Figure 4B:
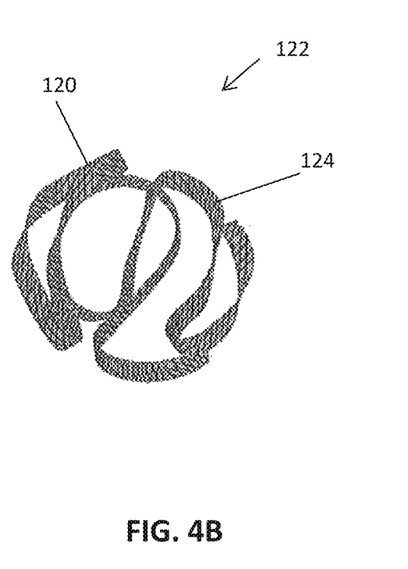
FIG. 4B illustrates the second three-dimensional structure of the embolic device of FIG. 1.

As shown in FIG. 4B, the second three-dimensional structure 122 comprises a series of seven (7) loops 124. The loops 124 may be open loops like that shown in the figure. Alternatively, one or more of the loops 124 may be closed-loops. In other embodiments, the second three-dimensional structure 122 may have more than seven loops (e.g., eight loops, nine loops, ten loops, eleven loops, twelve loops, etc.) or fewer than seven loops (e.g., six loops, five loops, four loops, etc.). In the illustrated embodiments, the loops 124 of the second three-dimensional structure 122 are connected by respective inflection points, which allow adjacent loops 124 to form reverse curvatures. In other embodiments, adjacent loops 124 of the second three-dimensional structure 122 may not form reverse curvatures. Furthermore, in other embodiments, instead of loops, the second three-dimensional structure 122 may have other structural elements with shapes that are not loops.

In some embodiments, a curvature of one of the loops 114 of the first three-dimensional structure 112 may be less than a curvature of one of the loops 124 of the second three-dimensional structure 122. For example, in one implementation, the curvature(s) of all of the loops 114 of the first three-dimensional structure 112 may be less than the curvature(s) of all of the loops 124 of the second three-dimensional structure 122. In another implementation, the curvature(s) of at least some of the loops 114 (e.g., a majority of the loops 114) of the first three-dimensional structure 112 may be less than the curvature(s) of at least some of the loops 124 (e.g., a majority of the loops 124) of the second three-dimensional structure 122. As used in this specification, "curvature" may be defined as 1/R, where R may be the smallest radius of curvature associated with the curve.

In some embodiments, the first three-dimensional structure 112 has at least two loops (e.g., at least two adjacent loops) with respective loop dimensions that do not vary by more than 20%, or that do not vary by more than 10%, or that do not vary by more than 5%. For example, in one implementation, the first three-dimensional structure 112 may have loops 114 with the same loop dimension (e.g., loop width or diameter). In other embodiments, the first three-dimensional structure 112 may have loops 114 with respective loop dimensions that vary by more than 20%.

In addition, in some embodiments, the loops 124 in the second three-dimensional structure 122 have respective loop dimensions that are less than the loop dimensions of the loops 114 in the first three-dimensional structure 112. This feature is advantageous because it assists the second segment 120 in forming the second three-dimensional structure 122 that is smaller than the first three-dimensional structure 112, thereby allowing the second three-dimensional structure 122 to fit within the first three-dimensional structure 112. In some cases, all of the loops 124 in the second three-dimensional structure 122 have respective loop dimensions that are less than the loop dimensions of all of the loops 114 in the first three-dimensional structure 112. In other cases, at least half or a majority of the loops 124 in the second three-dimensional structure 122 have respective loop dimensions that are less than the loop dimensions of at least half or a majority of the loops 114 in the first three-dimensional structure 112.

In some embodiments, the first segment 110 of the embolic device 100 may have a first width, and the second segment 120 of the embolic device 100 may have a second width that is less than the first width. Alternatively or additionally, the first segment 110 of the embolic device 100 may have a first thickness, and the second segment 120 of the embolic device 100 may have a second thickness that is less than the first thickness. In one implementation, the elongated member 102 may be a braided structure, and the narrower width and/or thickness of the second segment 120 may be accomplished by using fewer strands of fiber to form the braid for the second segment 120 compared to the number of strands of fiber used to form the braid for the first segment 110. Alternatively, the narrower width (or thickness) of the second segment 120 may be accomplished by cutting or grinding away (e.g., using laser cutter, grinder, etc.) some of the member that is used to form the second segment 120. As another alternative, the first and second segments 110, 120 may be formed from separate members with different respective cross-sectional dimensions. In such cases, the members may be secured to each other, e.g., using adhesive, weld, fusion, mechanical coupler, etc. It should be noted that the terms "width" and "thickness" may refer to the longer and shorter dimensions of a cross section in some cases, such as cross section having a rectangular shape or an elliptical shape. However, use of either of these terms should not imply that the cross section has an elongated shape. For example, width or thickness of a cross section may refer to a cross sectional dimension of a circular cross section, a square cross section, a hexagon cross section, a pentagon cross section, etc.

Also, in some embodiments, the first three-dimensional structure 112 has at least two adjacent loops 114 forming a first angle, and the second three-dimensional structure 122 has at least two adjacent loops 124 forming a second angle that is less than the first angle. This feature is advantageous because it assists the second segment 120 in forming the second three-dimensional structure 122 that is smaller than the first three-dimensional structure 112, thereby allowing the second three-dimensional structure 122 to fit within the first three-dimensional structure 112. In some embodiments, the angle between two adjacent loops 114 of the first three-dimensional structure 112 may correspond with a dimension of an aneurysm and/or with a curvature of a wall of the aneurysm. For example, the angle between two adjacent loops 114 of the first three-dimensional structure 112 may be configured such that the two adjacent loops 114 will engage against an inner wall of an aneurysm when the first three-dimensional structure 112 is delivered into the aneurysm. In some cases, all adjacent loops 114 in the first three-dimensional structure 112 form corresponding angles that correspond with a dimension of an aneurysm and/or with a curvature of a wall of the aneurysm. In other cases, at least half or a majority of the loops 114 in the first three-dimensional structure 112 form corresponding angles that correspond with a dimension of an aneurysm and/or with a curvature of a wall of the aneurysm. The above features allow the first three-dimensional structure 112 to have a shape that closely corresponds with a profile of an inner wall of an aneurysm. Accordingly, the first three-dimensional structure 112 provides a frame that fits around the perimeter of the inner wall of the aneurysm.

In some embodiments, all angles between pairs of adjacent loops 114 of the first three-dimensional structure 112 are the same, or do not vary by more than a certain percentage (e.g., 20%, 10%, 5%, etc.). In other embodiments, angles between two or more pairs of adjacent loops 114 may differ by more than 20%.

In addition, in some embodiments, the second segment 120 may have progressively reducing angles between adjacent loops 124 from distal end to proximal end of the second segment 120. This allows the second segment 120 to form the second three-dimensional structure 122 from "outside-towards-inside" so that an outer space within the aneurysm is filled first before the inner space in the aneurysm. In other embodiments, the second segment 120 may have progressively increasing angles between adjacent loops 124 from distal end to proximal end of the second segment 120. This allows the second segment 120 to form the second three-dimensional structure 122 from "inside-towards-outside" so that an inner space within the aneurysm is filled first before the outer space in the aneurysm.

In some embodiments, the elongated member 102 forming the first segment 110 and the second segment 120 of the embolic device 100 may be a braided structure. In such cases, each of the first segment 110 and the second segment 120 of the embolic device 100 comprises a braided segment. In one implementation, the first segment 110 and/or the second segment 120 may be formed by twenty-four strands of fibers that are braided. Alternatively, other numbers of strands of fibers may be used to form the elongated member. In another implementation, the first segment 110 may be formed using more strands compared to the second segment 120, thereby making the first segment 110 with a higher width and/or higher thickness compared to that of the second segment 120. In other embodiments, varying the number of strands may not change the width and/or thickness of the cross section. In further embodiments, the first segment 110 may be formed using more strands compared to the second segment 120, thereby making the first segment 110 stiffer compared to that of the second segment 120.

In other embodiments, the elongated member 102 forming the first segment 110 and the second segment 120 of the embolic device 100 may be a coil. In such cases, the elongated member 102 has a primary shape that is a coil, and the coil may then be bent to form a desired secondary shape.

In further embodiments, the elongated member 102 forming the first segment 110 and the second segment 120 of the embolic device 100 may be a solid continuous member. In such cases, the solid continuous member has a primary shape that is straight, and the solid continuous member may then be bent to form a desired secondary shape.

In one or more embodiments described herein, the combined length of the first and second segments 110, 120 may be anywhere from 15 cm to 50 cm, or from 25 cm to 45 cm, or from 30 to 40 cm. In other embodiments, the combined length of the first and second segments 110, 120 may be less than 15 cm or more than 40 cm.

Also, in one or more embodiments described herein, the elongated member 102 with the first and second segments 110, 120 may be made from any suitable materials. By means of non-limiting examples, the elongated member 102 of the embolic device 100 may be made from Nitinol®, AuPt, stainless steel, or other metals or alloys.

Figure 5A:
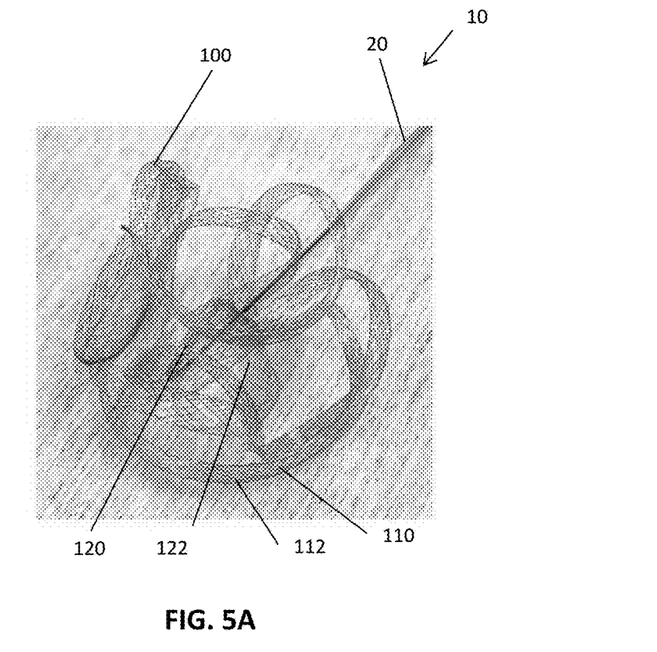
FIGS. 5A-5B illustrate a prototype of the medical device of FIG. 1.
Figure 5B:
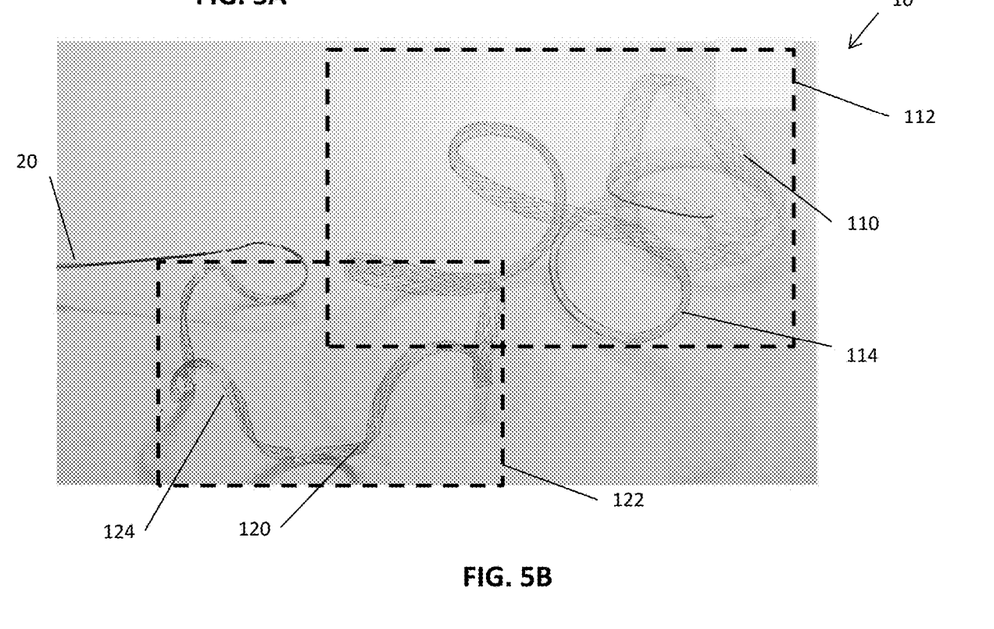

FIGS. 5A-5B illustrate a prototype of the medical device 10 of FIG. 1. As shown in FIG. 5A, the catheter 20 has delivered the first segment 110 forming the first three-dimensional structure 112, followed by the second segment 120 forming the second three-dimensional structure 122 inside the cavity of the first three-dimensional structure 112. FIG. 5B illustrates the same medical device 10 of FIG. 5A, with the second three-dimensional structure 122 placed outside the first three-dimensional structure 112, and stretched open to show the loops 114 of the first segment 110 and the loops 124 of the second segment 120.

Figure 6A:
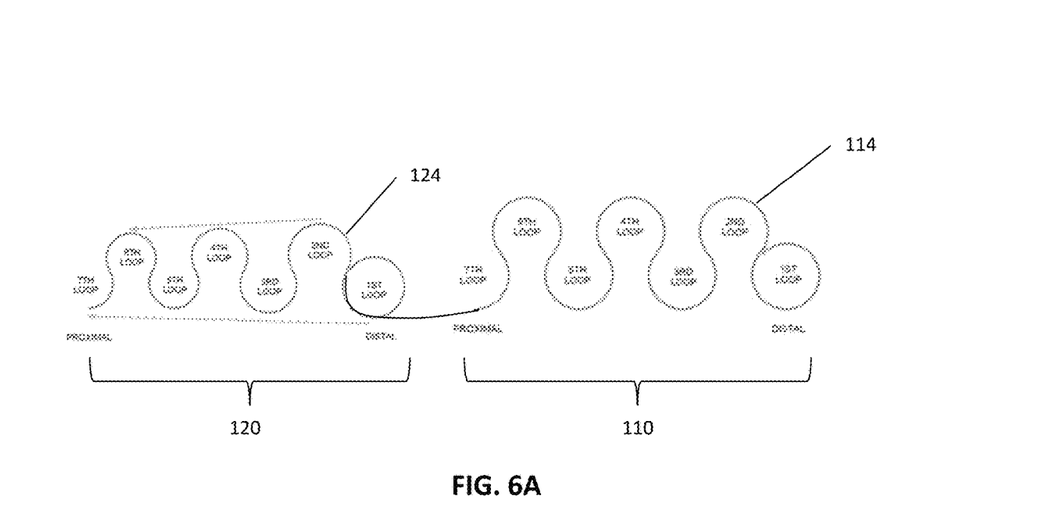
FIG. 6A illustrates an example of a loop-layout for the first and second segments of the embolic device of FIG. 1.

FIG. 6A illustrates an example of loop-layout for the first and second segments 110, 120 of the embolic device 100 of FIG. 1. In the illustrated example, the loops 114, 124 of the respective first segment 110 and the second segment 120 are presented in a plane so that the relative angle between the loops are not shown. This allows the relative sizes of the loops 114, 124 to be visualized. As shown in the example, the first segment 110 has seven loops, and the second segment 120 has seven loops. In other embodiments, the number of loops may be different. For example, in other embodiments, the first segment 110 may have more or fewer loops compared to the second segment 120. In the example, the sizes of the respective loops 124 in the second segment 120 decreases in the distal-to-proximal direction. This allows the aneurysm to be filled by the second segment 120 progressively from a perimeter of the aneurysm towards the inner core or center of the aneurysm as the second segment 120 is being pushed out of the catheter 20. In other embodiments, the sizes of the respective loops 124 in the second segment 120 may increase in the distal-to-proximal direction. This allows the aneurysm to be filled by the second segment 120 progressively from the inner core or center of the aneurysm towards the perimeter as the second segment 120 is being pushed out of the catheter 20. In further embodiments, the sizes of the respective loops 124 in the second segment 120 may be the same. In still further embodiments, the sizes of the loops 124 in the second segment 120 may vary up and down repeatedly, or may have a random pattern.

Figure 6B:
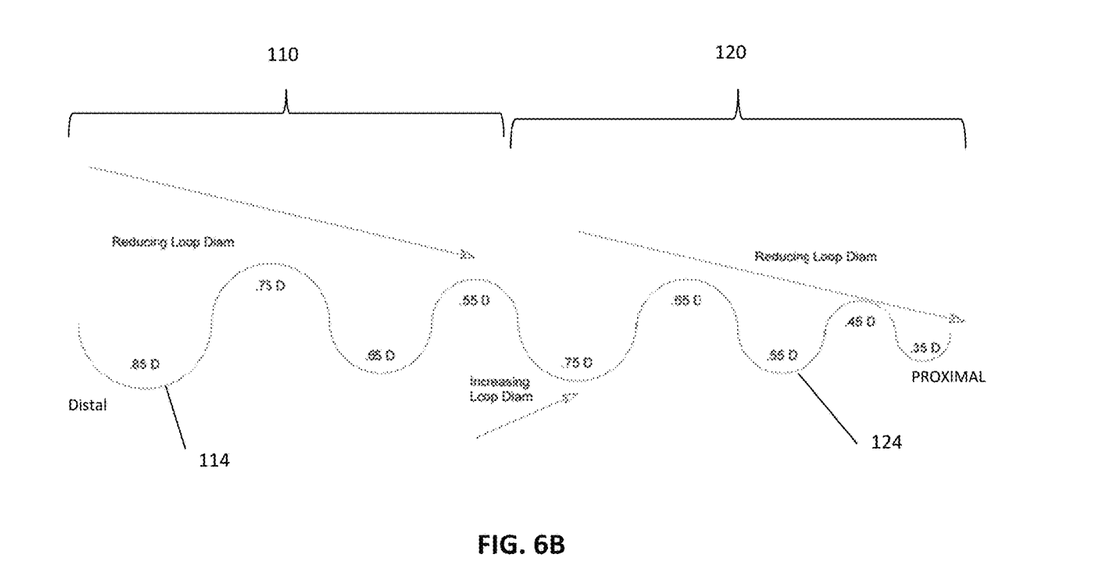
FIG. 6B illustrates another example of a loop-layout for the first and second segments of the embolic device of FIG. 1.

In the above example, the size of the first loop in the second segment 120 is the same or less than the size of the last loop in the first segment 110. In other example, the size of the first loop in the second segment 120 may be larger than the size of the last loop in the first segment 110. For example, as shown in FIG. 6B, the first segment 110 may have loops 114 with respective loop widths that decrease from 0.85 D to 0.55 D (wherein D may be a reference dimension), and the second segment 120 may have loops 124 with respective loop widths that decrease from 0.75 D to 0.35 D. This configuration is advantageous because the upsized larger loop (e.g., the loop with dimension of 0.75 D in the example) in the later segment may improve the packing by pushing out the previous loops (e.g., loops 0.65 D, 0.55 D in the example) in the previous segment (that has already been delivered) to the periphery of the aneurysm. In other embodiments, the embolic device 100 may include additional segments. For example, there may be a third segment that is proximal to the second segment 120, and the third segment may have a first loop with dimension of 0.55 D. Accordingly, as segments of the elongate member 102 are delivered, they form respective filling structures that radially push the previous delivered structure(s) radially towards the periphery of the aneurysm.

Although the embolic device 100 has been described as having the first segment 110 and the second segment 120, it should be noted that the embolic device 100 is not limited to having only two segments. In other embodiments, the embolic device 100 may have two or more segments. For example, in other embodiments, the embolic device 100 may have a third segment, a fourth segment, a fifth segment etc. In some embodiments, each previous segment form a filling structure that allows accommodation of later segment(s). This allows different three-dimensional structures to be progressively delivered into the aneurysm in a nesting configuration to fill the aneurysm from the periphery towards the center of the aneurysm. In some embodiments, the first segment 110 may have a first set of loops, the second segment 120 may have a second set of loops, the third segment may have a third set of loops, etc. The first set of loops may have loop widths that are the same in size, or that decrease in size in the distal-to-proximal direction. Similarly, the second set of loops may have loop widths that are the same in size, or that decrease in size in the distal-to-proximal direction. Also, the third set of loops may have loop widths that are the same in size, or that decrease in size in the distal-to-proximal direction. In addition, in some embodiments, the first (i.e., distal) loop in a subsequent segment may have a width that is smaller than a width of the last (i.e., proximal) loop in a previous segment. Alternatively, in other embodiments, the first (i.e., distal) loop in a subsequent segment may have a width that is larger than a width of the last (i.e., proximal) loop in a previous segment.

In one or more embodiments described herein, the embolic device 100 may optionally further include a distal loop at the distal end of the first segment 110, wherein the distal loop has a diameter that is 75% of less of the diameter of the loop proximal to the distal loop. In some embodiments, the distal loop may be formed by the first segment 110. As used in this specification, a "diameter" of a loop does not necessarily imply that the loop has a circular shape, and the term "diameter" may refer to a width of a loop, which may or may not be circular in shape. For example, a diameter of a loop may refer to a largest width of the loop in some cases.

Also, in one or more embodiments described herein, the embolic device 100 may optionally further include a distal coil at the distal end of the embolic device 100. In one implementation, if the first segment 110 is formed from a braid, the distal coil may be formed from one or more strands of the braid used to form the first segment 110. In another implementation, a separate coil may be provided as the distal coil, and is then attached to the distal end of the first segment 110.

In addition, in one or more embodiments described herein, the embolic device 100 may optionally further include a proximal coil at the proximal end of the embolic device 100. In one implementation, if the second segment 120 is formed from a braid, the proximal coil may be formed from one or more strands of the braid used to form the second segment 120. In another implementation, a separate coil may be provided as the proximal coil, and is then attached to the proximal end of the second segment 120. The proximal coil is advantageous because it may provide stiffness transition from the second segment 120 to the shaft 30.

Also, in one or more embodiments described herein, the second segment 120 of the embolic device 100 may have a stiffness (e.g., bending stiffness and/or axial stiffness) that is different from a stiffness (e.g., bending stiffness and/or axial stiffness) of the first segment 110 of the embolic device 100. In some embodiments, the second segment 120 may have a column strength that is different from a column strength of the first segment 110. For example, the column strength of the second segment 120 may be higher than a column strength of the first segment 110. This is advantageous because it allows the embolic device 100 to be pushed distally inside the catheter 20 without buckling. The relative difference in column strength and/or stiffness may be achieved using metallurgical heat treat condition, by variation in the cross-sectional dimension, and/or by varying number of strands in a braided structure, between the first and second segments 110, 120.

Also, in one or more embodiments described herein, if the member 102 forming the first and second segments 110, 120 is a braided structure, the braid angle of the strands along the length of the member 102 may be varied in order to change the stiffness along the length of the member 102. For example, in some embodiments, the first segment 110 and the second segment 120 may have the same number of strands, but the braid angle (e.g., angle formed by the strands with respect to the longitudinal axis of the member 102) of the strands in the first segment 110 may be larger than the braid angle of the strands in the second segment 120, thereby making the first segment 110 stiffer than the second segment 120. In other embodiments, the braid angle of the strands in the second segment 120 may be larger than the braid angle of the strands in the first segment 110, thereby making the second segment 120 stiffer than the first segment 110. Also, in some embodiments, the braid angle of the strands along the length of the member 102 may vary gradually.

In addition, in some embodiments, the first three-dimensional structure 112 comprises a first plurality of loops 114, and wherein loop widths, loop curvatures, braid widths, braid thicknesses, braid angles, or any combination of the foregoing, of the respective ones of the first plurality of loops 114 increase or decrease along a length of the first segment 110 forming the first three-dimensional structure 112; and/or wherein the second three-dimensional structure 122 comprises a second plurality of loops 124, and wherein loop widths, loop curvatures, braid widths, braid thicknesses, braid angles, or any combination of the foregoing, of the respective ones of the second plurality of loops 124 increase or decrease along a length of the second segment 120 forming the second three-dimensional structure 122.

In addition, in some embodiments, the first three-dimensional structure 112 comprises a first plurality of loops 114, and wherein angles between adjacent ones of the first plurality of loops 114 increase or decrease along a length of the first segment 110 forming the first three-dimensional structure 112; and/or wherein the second three-dimensional structure 122 comprises a second plurality of loops 124, and wherein angles between adjacent ones of the second plurality of loops 124 increase or decrease along a length of the second segment 120 forming the second three-dimensional structure 122.

Furthermore, it should be noted that the embolic device 100 is not limited to the examples described herein, and that the embolic device 100 may have other configurations in other embodiments. For example, in other embodiments, the first segment 110 of the embolic device 100 may have other curved shapes as long as it forms a framing structure to define a cavity therein. Also, in other embodiments, the second segment 120 of the embolic device 100 may have other curved shapes as long as it provides a central filling effect to fill the central cavity defined by the first three-dimensional structure formed by the first segment 110.

Various techniques may be used to form the embolic device 100. In some embodiments, the elongated member 102 may be wrapped around one or more mandrels to form a desired shape. The mandrel(s) may include multiple posts configured to allow the elongated member 102 to wrap there-around. The sizes of the posts will dictate the loop sizes of the loops to be formed. Also, the relative orientation of the posts will dictate the relative angles among the loops to be formed. After the elongated member 102 has been wrapped around the mandrel(s), the elongated member 102 may be chemically treated and/or heat treated to set the shape of the elongated member 102. Other techniques for shaping an elongated member may be used in other embodiments to form the embolic device 100.

Figure 7A:
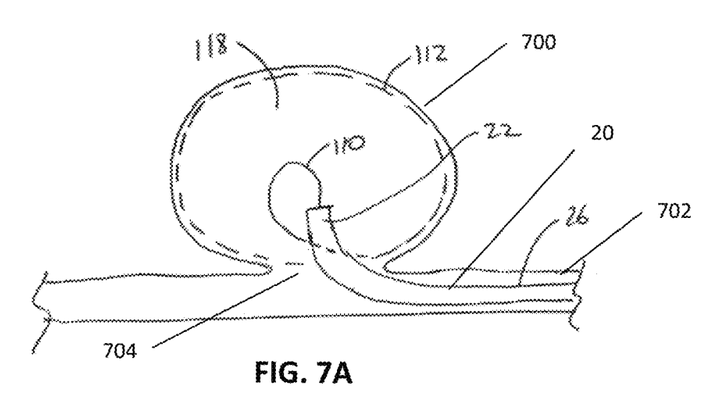
FIGS. 7A-7B illustrate a method of using the medical device of FIG. 1.
Figure 7B:
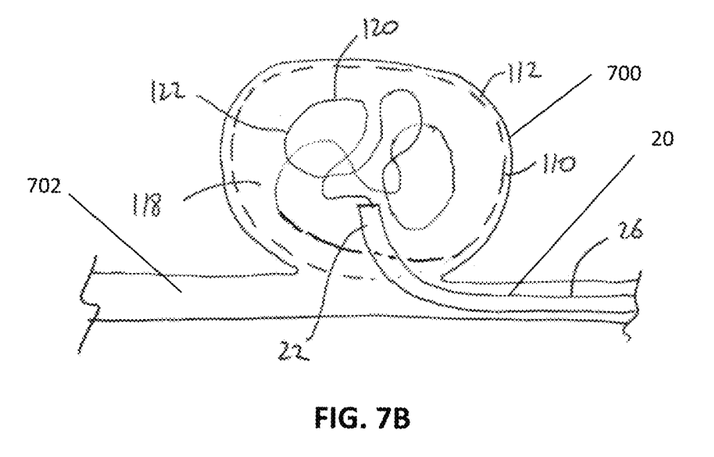

FIGS. 7A-7B illustrate a method of using the medical device 10 of FIG. 1 to treat an aneurysm 700. When using the medical device 10, the catheter 20 is first inserted into a blood vessel 702 of a patient through an incision. The catheter 20 is then advanced distally until the distal end 22 of the catheter 20 is at the aneurysm.

In some embodiments, the catheter 20 may be steerable. For example, the catheter 20 may include one or more steering wires configured to steer the distal end 22 of the catheter 20 in one or more directions. In other embodiments, the catheter 20 may not be steerable. Instead, a guidewire may first be used to access the target site. Then the catheter 20 may be disposed over the guidewire, and advanced distally using the guidewire. In such cases, the catheter 20 may include a separate channel for accommodating the guidewire.

After the distal end 22 of the catheter 20 is desirably placed, the shaft 30 (shown in FIG. 1) is then advanced to push the embolic device 100 distally until the first segment 110 of the embolic device 100 is outside the catheter 20 (FIG. 7A). As shown in the figure, the first segment 110 forms the first three-dimensional structure 112 when the first segment 110 is unconfined outside the catheter 20. The first three-dimensional structure 112 has a shape that corresponds with an inner wall of the aneurysm such that the first three-dimensional structure 112 is positioned closely next to (e.g., against or within 0.5 mm from) the wall of the aneurysm. The first three-dimensional structure 112, represented schematically by the dashed line in FIG. 7A, provides a frame defining the cavity 118 for accommodating the second segment 120 of the embolic device 100. As shown in the figure, the first three-dimensional structure 112 also provides a scaffolding across a neck 704 of an aneurysm 700, which assists in containing the second-dimensional structure 122 to be delivered into the cavity 118.

Next, the shaft 30 may be advanced further to push the second segment 120 of the embolic device 100 until the second segment 120 is out of the catheter 20 (FIG. 7B). As shown in the figure, the second segment 120 forms the second three-dimensional structure 122 when the second segment 120 is unconfined outside the catheter 20. The second three-dimensional structure 122 has a shape that allows it to fill at least some of the space in the cavity 118 defined by the first three-dimensional structure 112. As shown in the figure, the scaffolding across the neck 704 of the aneurysm provided by the first three-dimensional structure 112 prevents the second-dimensional structure 122 from escaping or falling out of the cavity 118 of the first three-dimensional structure 112 and out of the aneurysm.

In some embodiments, the distal end of the shaft 30 abuts against the proximal end of the second segment 120, and is not mechanically attached to the proximal end of the second segment 120. In such cases, the second segment 120 becomes decoupled from the remaining part of the medical device 10 as soon as the proximal end of the second segment 120 is pushed out of the catheter 20. In other embodiments, the distal end of the shaft 30 may be mechanically connected to the proximal end of the second segment 120, such as via a mechanical connector that is operable to disengage the proximal end of the second segment 120 from the shaft 30. In further embodiments, the distal end of the shaft 30 may be mechanically connected to the proximal end of the second segment 120 via a disintegratable link, such as a link that can be disintegrated in response to application of a current. Mechanical connectors and disintegratable links are well known in the art, and therefore will not be described in further detail.

In some embodiments, multiple embolic devices 100 may be provided with different respective lengths. In such cases, before one of the embolic devices 100 is selected for treating an aneurysm, a doctor may measure a size of the aneurysm to be treated. For example, the doctor may perform measurement using one or more images of the aneurysm to determine the size of the aneurysm. The size may be a cross-sectional dimension of the aneurysm, a cross-sectional area of the aneurysm, a volume of the aneurysm, etc. After a size of the aneurysm has been determined, one of the embolic devices 100 may then be selected based on the size of the aneurysm. For example, a longer embolic device 100 may be selected to occlude a larger aneurysm.

As illustrated in the above example, the embolic device 100 is advantageous because the same device can achieve the dual purposes of (1) forming a frame at the perimeter of the aneurysm that provides a scaffolding across the neck of the aneurysm, and (2) filling the central space of the aneurysm while ensuring that the filling is contained by the frame inside the aneurysm. The embolic device 100 may be used to treat all types of aneurysm, including those with wide necks. The embolic device 100 is also advantageous because it does not require multiple deliveries of separate embolic devices. In particular, because the same embolic device 100 provides both framing and filling purposes, it obviates the need to provide multiple deliveries—with one delivery for the framing, and other deliveries of separate device(s) for filling. Furthermore, the features of the embolic device 100 described herein are advantageous because they allow delivery of a long member into an aneurysm through progressive nesting action in which different parts of the elongated member 102 are configured to form different layers of "nest" as the elongated member 102 is delivered outside the delivery catheter. This in turn allows the aneurysm to be substantially and/or tightly filled by the embolic device 100.

Figure 8:
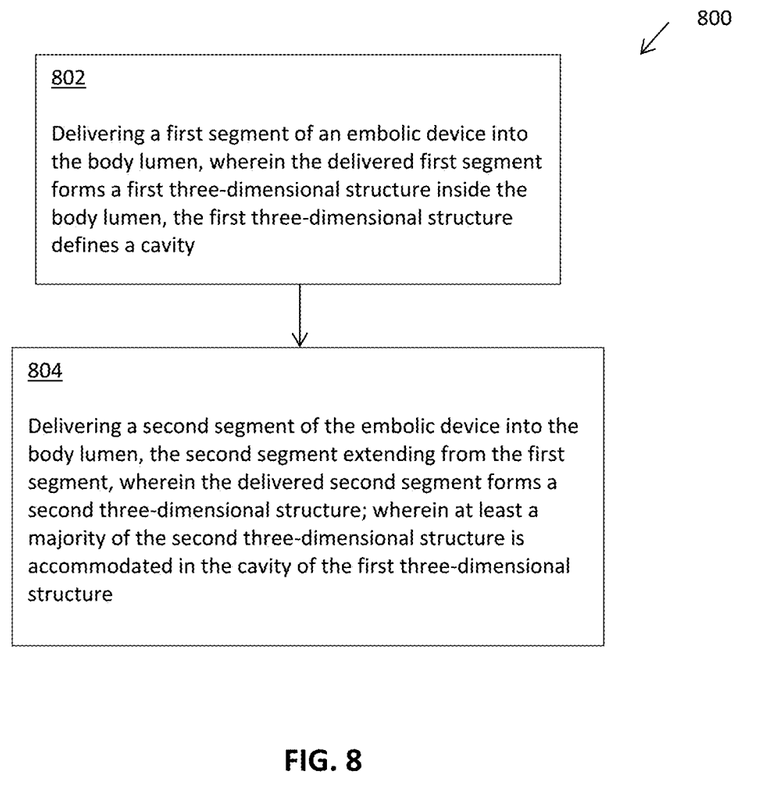
FIG. 8 illustrates a method of delivering an embolic device into an aneurysm.

FIG. 8 illustrates a method 800 of occluding a body lumen. The method 800 includes delivering a first segment of an embolic device into the body lumen, wherein the delivered first segment forms a first three-dimensional structure inside the body lumen, the first three-dimensional structure defines a cavity (item 802). The method 800 also includes delivering a second segment of the embolic device into the body lumen, the second segment extending from the first segment, wherein the delivered second segment forms a second three-dimensional structure; wherein at least a majority of the second three-dimensional structure is accommodated in the cavity of the first three-dimensional structure (item 804).

In some embodiments, the embolic device in the method 800 may be the embolic device 100 described herein.

Optionally, in the method 800, the first three-dimensional structure comprises a first loop, and the second three-dimensional structure comprises a second loop, Optionally, in the method 800, a first curvature of the first loop of the first three-dimensional structure is less than a second curvature of the second loop of the second three-dimensional structure.

Optionally, in the method 800, the first segment has a first width, and the second segment has a second width that is less than the first width; and/or wherein the first segment has a first thickness, and the second segment has a second thickness that is less than the first thickness.

Optionally, in the method 800, the first segment and the second segment form a unity configuration.

Optionally, in the method 800, each of the first segment and the second segment comprises a braided segment.

Optionally, in the method 800, the first three-dimensional structure comprises a first plurality of loops, and wherein loop widths, loop curvatures, braid widths, braid thicknesses, braid angles, or any combination of the foregoing, of the respective ones of the first plurality of loops increase or decrease along a length of the first segment forming the first three-dimensional structure; and/or wherein the second three-dimensional structure comprises a second plurality of loops, and wherein loop widths, loop curvatures, braid widths, braid thicknesses, braid angles, or any combination of the foregoing, of the respective ones of the second plurality of loops increase or decrease along a length of the second segment forming the second three-dimensional structure.

Optionally, in the method 800, the first three-dimensional structure comprises a first plurality of loops, and wherein angles between adjacent ones of the first plurality of loops increase or decrease along a length of the first segment forming the first three-dimensional structure; and/or wherein the second three-dimensional structure comprises a second plurality of loops, and wherein angles between adjacent ones of the second plurality of loops increase or decrease along a length of the second segment forming the second three-dimensional structure.

Optionally, in the method 800, the first three-dimensional structure provides a scaffolding across a neck of an aneurysm.

Optionally, in the method 800, the first three-dimensional structure has at least two adjacent loops with respective loop dimensions that do not vary by more than 20%, or that do not vary by more than 10%, or that do not vary by more than 5%.

Optionally, in the method 800, the first three-dimensional structure has at least two adjacent loops forming a first angle, and wherein the second three-dimensional structure has at least two adjacent loops forming a second angle that is less than the first angle.

Optionally, in the method 800, the first segment and the second segment are parts of an elongated member having a distal end and a proximal end.

The following items are exemplary features of embodiments described herein. Each item may be an embodiment itself or may be a part of an embodiment. One or more items described below may be combined with other item(s) in an embodiment.

Item 1: An embolic device for placement in a body lumen, includes: a first segment having a first linear configuration when located inside a catheter, the first segment being configured to form a first three-dimensional structure when outside the catheter, wherein the first three-dimensional structure defines a cavity; and a second segment extending from the first segment, the second segment having a second linear configuration when located inside the catheter, the second segment being configured to form a second three-dimensional structure when outside the catheter; wherein the cavity of the first three-dimensional structure is configured to accommodate at least a majority of the second three-dimensional structure.

Item 2: The first three-dimensional structure comprises a first loop, and the second three-dimensional structure comprises a second loop, Item 3: A first curvature of the first loop of the first three-dimensional structure is less than a second curvature of the second loop of the second three-dimensional structure.

Item 4: The first segment has a first width, and the second segment has a second width that is less than the first width; and/or wherein the first segment has a first thickness, and the second segment has a second thickness that is less than the first thickness.

Item 5: The first segment and the second segment form a unity configuration.

Item 6: Each of the first segment and the second segment comprises a braided segment.

Item 7: The first three-dimensional structure comprises a first plurality of loops, and wherein loop widths, loop curvatures, braid widths, braid thicknesses, braid angles, or any combination of the foregoing, of the respective ones of the first plurality of loops increase or decrease along a length of the first segment forming the first three-dimensional structure; and/or wherein the second three-dimensional structure comprises a second plurality of loops, and wherein loop widths, loop curvatures, braid widths, braid thicknesses, braid angles, or any combination of the foregoing, of the respective ones of the second plurality of loops increase or decrease along a length of the second segment forming the second three-dimensional structure.

Item 8: The first three-dimensional structure comprises a first plurality of loops, and wherein angles between adjacent ones of the first plurality of loops increase or decrease along a length of the first segment forming the first three-dimensional structure; and/or wherein the second three-dimensional structure comprises a second plurality of loops, and wherein angles between adjacent ones of the second plurality of loops increase or decrease along a length of the second segment forming the second three-dimensional structure.

Item 9: The first three-dimensional structure has at least two adjacent loops forming a first angle, and wherein the second three-dimensional structure has at least two adjacent loops forming a second angle that is less than the first angle.

Item 10: The first segment and the second segment are parts of an elongated member having a distal end and a proximal end.

Item 11: An embolic device for placement in a body lumen, includes: an elongated member having a proximal end and a distal end; wherein the elongated member comprises a first segment configured to form a first three-dimensional structure, wherein the first three-dimensional structure defines a cavity; and wherein the elongated member comprises a second segment configured to form a second three-dimensional structure inside the cavity of the first three-dimensional structure.

Item 12: The first three-dimensional structure formed by the first segment of the elongated member comprises a first loop, and the second three-dimensional structure formed by the second segment of the elongated member comprises a second loop, Item 13: A first curvature of the first loop of the first three-dimensional structure is less than a second curvature of the second loop of the second three-dimensional structure.

Item 14: The first segment has a first width, and the second segment has a second width that is less than the first width; and/or wherein the first segment has a first thickness, and the second segment has a second thickness that is less than the first thickness.

Item 15: The first segment and the second segment form a unity configuration.

Item 16: Each of the first segment and the second segment comprises a braided segment.

Item 17: The first three-dimensional structure comprises a first plurality of loops, and wherein loop widths, loop curvatures, braid widths, braid thicknesses, braid angles, or any combination of the foregoing, of the respective ones of the first plurality of loops increase or decrease along a length of the first segment forming the first three-dimensional structure; and/or wherein the second three-dimensional structure comprises a second plurality of loops, and wherein loop widths, loop curvatures, braid widths, braid thicknesses, braid angles, or any combination of the foregoing, of the respective ones of the second plurality of loops increase or decrease along a length of the second segment forming the second three-dimensional structure.

Item 18: The first three-dimensional structure comprises a first plurality of loops, and wherein angles between adjacent ones of the first plurality of loops increase or decrease along a length of the first segment forming the first three-dimensional structure; and/or wherein the second three-dimensional structure comprises a second plurality of loops, and wherein angles between adjacent ones of the second plurality of loops increase or decrease along a length of the second segment forming the second three-dimensional structure.

Item 19: The first three-dimensional structure has at least two adjacent loops forming a first angle, and wherein the second three-dimensional structure has at least two adjacent loops forming a second angle that is less than the first angle.

Item 20: A method of occluding a body lumen includes: delivering a first segment of an embolic device into the body lumen, wherein the delivered first segment forms a first three-dimensional structure inside the body lumen, the first three-dimensional structure defines a cavity; and delivering a second segment of the embolic device into the body lumen, the second segment extending from the first segment, wherein the delivered second segment forms a second three-dimensional structure; wherein at least a majority of the second three-dimensional structure is accommodated in the cavity of the first three-dimensional structure.

Item 21: The first three-dimensional structure comprises a first loop, and the second three-dimensional structure comprises a second loop, Item 22: A first curvature of the first loop of the first three-dimensional structure is less than a second curvature of the second loop of the second three-dimensional structure.

Item 23: The first segment has a first width, and the second segment has a second width that is less than the first width; and/or wherein the first segment has a first thickness, and the second segment has a second thickness that is less than the first thickness.

Item 24: The first segment and the second segment form a unity configuration.

Item 25: Each of the first segment and the second segment comprises a braided segment.

Item 26: The first three-dimensional structure provides a scaffolding across a neck of an aneurysm.

Item 27: The first three-dimensional structure has at least two adjacent loops with respective loop dimensions that do not vary by more than 20%, or that do not vary by more than 10%, or that do not vary by more than 5%.

Item 28: The first three-dimensional structure has at least two adjacent loops forming a first angle, and wherein the second three-dimensional structure has at least two adjacent loops forming a second angle that is less than the first angle.

Item 29: The first segment and the second segment are parts of an elongated member having a distal end and a proximal end.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

The invention claimed is:

1. An embolic device for placement in a body lumen, the embolic device comprising:
    a first segment having a first curvilinear configuration with a first curvature when located inside a catheter, the first segment being configured to form a first three-dimensional structure when outside the catheter; and
    a second segment extending from the first segment, the second segment having a second curvilinear configuration when located inside the catheter, the second segment being configured to form a second three-dimensional structure when outside the catheter;
    wherein the first segment has a cross section with a first cross-sectional width measured in a direction that is perpendicular to a first longitudinal axis of the first segment when the first segment is inside the catheter;
    wherein the first segment is configured to go through a first change and a second change when the first segment is outside the catheter, wherein in the first change, the cross-section of the first segment increases from the first cross-sectional width to a second cross-sectional width greater than the first cross-sectional width, and wherein in the second change, the first segment changes shape to have a second curvature higher than the first curvature, and
    wherein the first segment configured to form the first three-dimensional structure is distal to the second segment configured to form the second three-dimensional structure when the embolic device is inside the catheter such that the first segment is configured to exit the catheter in the body lumen before the second segment, wherein the first three-dimensional structure formed by the first segment comprises at least two non-parallel first loops, wherein the second three-dimensional structure formed by the second segment comprises at least two non-parallel second loops, and wherein each of the first non-parallel first loops of the first three-dimensional structure is larger than the non-parallel second loops of the second three-dimensional structure.

2. The embolic device of claim 1, wherein a first loop curvature of one of the first loops of the first three-dimensional structure is less than a second loop curvature of one of the second loops of the second three-dimensional structure.

3. The embolic device of claim 1, wherein the first segment has a first thickness, and the second segment has a second thickness that is less than the first thickness.

4. The embolic device of claim 1, wherein the first segment and the second segment form a unity configuration.

5. The embolic device of claim 1, wherein loop widths, braid widths, braid thicknesses, braid angles, or any combination of the foregoing, of the respective ones of the first loops increase or decrease along a length of the first segment forming the first three-dimensional structure; and/or
    wherein loop widths, braid widths, braid thicknesses, braid angles, or any combination of the foregoing, of the respective ones of the second loops increase or decrease along a length of the second segment forming the second three-dimensional structure.

6. The embolic device of claim 1, wherein the at least two non-parallel first loops comprise at least four first loops L1, L2, L3, L4 with different respective pitch angles; and/or
    wherein the at least two non-parallel second loops comprise at least four second loops L'1, L'2, L'3, L'4 with different respective pitch angles.

7. The embolic device of claim 1, wherein the at least two non-parallel first loops of the first three-dimensional structure form a first angle, and wherein the at least two non-parallel second loops of the second three-dimensional structure form a second angle that is less than the first angle.

8. The embolic device of claim 1, wherein the first longitudinal axis of the first segment extends through a first body structure of the first segment.

9. The embolic device of claim 1, wherein the first segment comprises a flat braided segment extending continuously at least along a majority of a longitudinal length of the first segment, and wherein a major plane of the flat braided segment is parallel to the first longitudinal axis of the first segment when the first segment is outside the catheter.

10. An embolic device for placement in a body lumen, the embolic device comprising:
    a first segment having a first linear configuration when located inside a catheter, the first segment being configured to form a first three-dimensional structure when outside the catheter; and
    a second segment extending from the first segment, the second segment having a second linear configuration when located inside the catheter, the second segment being configured to form a second three-dimensional structure when outside the catheter;
    wherein the first segment comprises a first braided segment forming at least a majority of the first three-dimensional structure, and the second segment comprises a second braided segment forming at least a majority of the second three-dimensional structure;
    wherein the first braided segment is distal to the second braided segment when the first braided segment and the second braided segment are inside the catheter such that the first braided segment is configured to exit the catheter in the body lumen before the second braided segment, wherein the first braided segment has a maximum cross-sectional width that is larger than a maximum cross-sectional width of the second braided segment when the first braided segment and the second braided segment is outside the catheter, and wherein the first braided segment has a flat cross-sectional shape when the first braided segment is outside the catheter;

wherein the first three-dimensional structure configured to be formed by the first braided segment that is distal to the second braided segment comprises at least two non-parallel first loops, wherein the second three-dimensional structure configured to be formed by the second braided segment comprises at least two non-parallel second loops, wherein each of the non-parallel first loops is larger than the non-parallel second loops.

11. The embolic device of claim 10, wherein the maximum cross-sectional width of the first braided segment is measured in a direction that is perpendicular to a longitudinal axis of the first braided segment.

12. The embolic device of claim 10, wherein the first braided segment comprises a flat braided segment extending continuously at least along a majority of a longitudinal length of the first braided segment, and wherein a major plane of the flat braided segment is parallel to a longitudinal axis of the first segment when the first segment is outside the catheter.

13. An embolic device for placement in a body lumen, the embolic device comprising:

an elongated member having a proximal end and a distal end;

wherein the elongated member comprises a first segment configured to form a first three-dimensional structure;

wherein the elongated member comprises a second segment configured to form a second three-dimensional structure;

wherein the first segment comprises a first braided segment forming at least a majority of the first three-dimensional structure, and the second segment comprises a second braided segment forming at least a majority of the second three-dimensional structure; and wherein the first braided segment of the elongated member is distal to the second braided segment of the elongated member when the elongated member is inside a catheter such that the first braided segment is configured to exit the catheter in the body lumen before the second braided segment, wherein the first braided segment comprises a first flat braided segment forming at least three non-parallel first braided loops when the first segment is outside the catheter, wherein the second braided segment comprises a second flat braided segment forming at least three non-parallel second braided loops when the second segment is outside the catheter, and wherein each of the non-parallel first braided loops is larger than the non-parallel second braided loops.

14. The embolic device of claim 13, wherein a first loop curvature of one of the non-parallel first braided loops of the first three-dimensional structure is less than a second loop curvature of one of the non-parallel second braided loops of the second three-dimensional structure.

15. The embolic device of claim 13, wherein the first segment has a first thickness, and the second segment has a second thickness that is less than the first thickness.

16. The embolic device of claim 13, wherein the first segment and the second segment form a unity configuration.

17. The embolic device of claim 13, wherein loop widths, braid widths, braid thicknesses, braid angles, or any combination of the foregoing, of the respective ones of the at least three non-parallel first braided loops increase or decrease along a length of the first segment forming the first three-dimensional structure; and/or wherein loop widths, braid widths, braid thicknesses, braid angles, or any combination of the foregoing, of the respective ones of the at least three non-parallel second braided loops increase or decrease along a length of the second segment forming the second three-dimensional structure.

18. The embolic device of claim 13, wherein the at least three non-parallel first braided loops of the first three-dimensional structure comprise at least four first loops L1, L2, L3, L4 with different respective pitch angles; and/or wherein the at least three non-parallel second braided loops of the second three-dimensional structure comprise at least four second loops L'1, L'2, L'3, L'4 with different respective pitch angles.

19. The embolic device of claim 13, wherein two of the non-parallel first braided loops of the first three-dimensional structure form a first angle, and wherein two of the non-parallel second braided loops of the second three-dimensional structure form a second angle that is less than the first angle.

20. The embolic device of claim 13, wherein the first flat braided segment extends continuously at least along a majority of a longitudinal length of the first segment, and wherein a major plane of the first flat braided segment is parallel to a longitudinal axis of the first segment when the first segment is outside the catheter.

* * * * *